United States Patent [19]
Atherton et al.

[11] Patent Number: 6,028,219
[45] Date of Patent: Feb. 22, 2000

[54] PROCESS FOR THE NITRATION OF DIPHENYLETHERS

[75] Inventors: John Heathcote Atherton, Huddersfield; Stephen Martin Brown, Upper Cumberworth; James Peter Muxworthy; Martin Lennon, both of Huddersfield, all of United Kingdom

[73] Assignee: Zeneca Limited, London, United Kingdom

[21] Appl. No.: 08/901,545

[22] Filed: Jul. 28, 1997

Related U.S. Application Data

[63] Continuation-in-part of application No. 08/712,695, Sep. 11, 1996.

[30] Foreign Application Priority Data

Sep. 13, 1995 [GB] United Kingdom .................... 9518705

[51] Int. Cl.[7] ................................................. C07C 205/06
[52] U.S. Cl. ........................... 562/435; 560/21; 562/434; 564/99; 564/166; 568/585
[58] Field of Search .............. 560/21; 562/435, 562/434; 568/585; 564/166, 99

[56] References Cited

U.S. PATENT DOCUMENTS

| | | | |
|---|---|---|---|
| 4,031,131 | 6/1977 | Johnson | 260/473 |
| 4,400,530 | 8/1983 | Grove | 560/21 |
| 4,424,393 | 1/1984 | Guzik et al. | 560/21 |
| 4,429,146 | 1/1984 | Liu | 560/21 |
| 4,594,440 | 6/1986 | Giacobbe et al. | 560/21 |
| 4,743,703 | 5/1988 | Swithenbank | 560/21 |

FOREIGN PATENT DOCUMENTS

| | | |
|---|---|---|
| 003416 | 8/1979 | European Pat. Off. |
| 022610 | 1/1981 | European Pat. Off. |
| 114299 | 8/1984 | European Pat. Off. |
| 147798 | 7/1985 | European Pat. Off. |
| 274194 | 7/1988 | European Pat. Off. |
| 668260 | 8/1995 | European Pat. Off. |
| 332 28 17 | 6/1985 | Germany. |
| 1419209 | 12/1975 | United Kingdom. |
| 1478428 | 6/1977 | United Kingdom. |
| 2103214A | 2/1983 | United Kingdom. |
| 2152817 | 8/1985 | United Kingdom. |
| 2154235 | 9/1985 | United Kingdom. |
| 2205749 | 12/1988 | United Kingdom. |
| 94/19310 | 9/1994 | WIPO. |
| 9419310 | 9/1994 | WIPO. |
| WO 98/19978 | 5/1998 | WIPO. |

Primary Examiner—Shailendra Kumar

Attorney, Agent, or Firm—Dianne Burkhard

[57] ABSTRACT

A process for the preparation of a compound of general formula I:

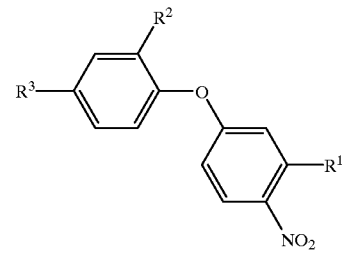

wherein:
$R^1$ is hydrogen or $C_1$–$C_6$ alkyl, $C_2$–$C_6$ alkenyl or $C_2$–$C_6$ alkynyl, any of which may optionally be substituted with one or more substituents selected from halogen and OH; or $COOR^4$, $COR^6$, $CONR^4R^5$ or $CONHSO_2R^4$;

$R^4$ and $R^5$ are each independently hydrogen or $C_1$–$C_4$ alkyl optionally substituted with one or more halogen atoms;

$R^6$ is a halogen atom or a group $R^4$;

$R^2$ is hydrogen or halo;

$R^3$ is $C_1$–$C_4$ alkyl, $C_2$–$C_4$ alkenyl or $C_2$–$C_4$ alkynyl, any of which may optionally be substituted with one or more halogen atoms; or halo;

the process comprising reacting a compound of general formula II:

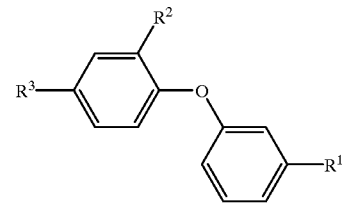

wherein $R^1$, $R^2$ and $R^3$ are as defined for general formula I; with a nitrating agent comprising nitric acid or a mixture of nitric and sulphuric acids in the presence of an organic solvent and in the presence of acetic anhydride, characterized in that the molar ratio of acetic anhydride to compound of general formula II is from about 1:1 to 3:1.

12 Claims, No Drawings

PROCESS FOR THE NITRATION OF DIPHENYLETHERS

This application is a continuation-in-part of U.S. patent application Ser. No. 08/712,695, filed on Sep. 11, 1996.

The present invention relates to a process for nitration and, in particular to a process for nitrating diphenyl ether compounds which are useful as herbicides or as intermediates in the synthesis of herbicides.

EP-A-0022610 relates to herbicides of the formula:

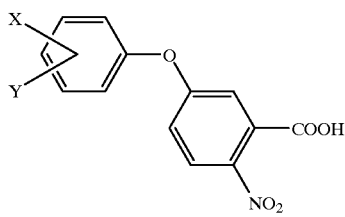

wherein X and Y may be H, F, Cl, Br, $CF_3$, $OCF_2CHZ_2$ (Z=Cl, Br, F), $OCH_3$, CN, $CO_2R$ (R=lower alkyl), $C_6H_5$, O-alkyl, $NO_2$ or $SO_2$ lower alkyl; and also describes a process for making these compounds by nitrating a compound of the formula:

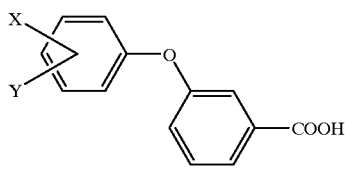

wherein X and Y are as defined above.

Suggested nitrating agents for this reaction include mixtures of nitric and sulphuric acids and the recommended reaction solvent is dichloromethane. The nitration process is said to give a yield of 75.4% but no details are given of the purity of the product or the presence of other nitrated isomers.

U.S. Pat. No. 4,031,131 describes similar compounds to the above which are prepared in a similar manner. Suggested nitrating agents include potassium nitrate or mixed nitric and sulphuric acids and the reaction is carried out in dichloromethane. An extremely high yield (>95%) is claimed for the nitration reaction but, again, there are no details given about the purity of the product. Nitration reactions using mixed nitric and sulphuric acids may also be carried out in the presence of acetic anhydride.

EP-A-0003416 and EP-A-0274194 both relate to the synthesis of herbicidal compounds of the formula:

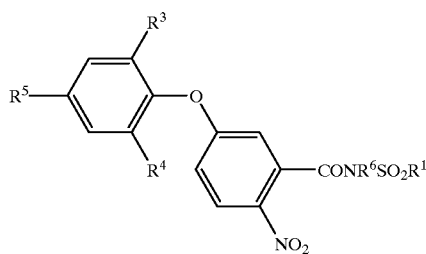

wherein $R^1$ is alkyl optionally substituted with fluorine or optionally substituted phenyl;

$R^3$ is H, F, Cl, Br, I, alkyl, trifluoromethyl or CN;
$R^4$ is H, F, Cl, Br, I or trifluoromethyl;
$R^5$ is F, Cl, Br, I or trifluoromethyl; and
$R^6$ is H or $C_1$–$C_4$ alkyl.

In EP-A-0003416, these compounds may be obtained by nitrating the corresponding carboxylic acid or carboxamide and then converting to the sulphonamide, or by nitrating the sulphonamide itself. A nitration reaction is described in Example 7 where the solvent is 1,2-dichloroethane and the nitrating agent is a mixture of potassium nitrate and concentrated sulphuric acid.

EP-A-0274194 relates, in particular, to a process for the nitration of compounds of the formula:

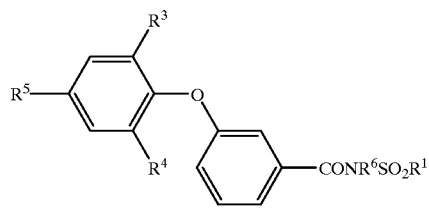

The nitration reaction is said to be carried out using a conventional nitrating agent such as concentrated nitric acid or sodium nitrate or mixtures of these with sulphuric acid. The reaction solvent is one which is resistant to nitration and examples of such solvents are said to include halogenated solvents such as dichloromethane, dichloroethane, dichloropropane, chlorofluorocarbons and aromatic solvents such as nitrobenzene.

However, none of these methods are particularly satisfactory for use on an industrial scale because they all have the common problem that the reaction yields a mixture of the required product and other nitrated isomers. Nitrated isomers of diphenyl ether compounds are often extremely difficult to separate from one another and the quantity of other isomers is often too high for the final product to fulfil the requirements of the regulatory authorities for herbicides. The problem tends to be further exacerbated if the nitrated product is an intermediate in the synthesis of a herbicide rather than the required herbicide itself, because the mixture of nitrated compounds means that larger quantities of other reagents must be used than would be necessary if the nitrated isomers could be separated satisfactorily. It is therefore important to ensure that the nitration process produces a product mixture containing the highest possible proportion of the desired isomer.

The problem of obtaining mixtures of isomers from the nitration process was recognised by the authors of GB-A-2103214 who describe a process in which a compound of the formula:

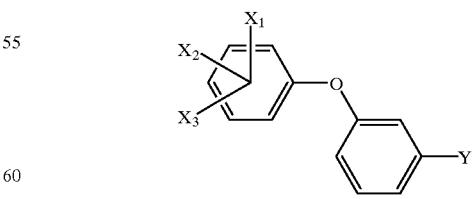

wherein each of $X_1$, $X_2$ and $X_3$ is H, F, Cl, Br, $CF_3$, $OCF_2CHZ_2$ (where Z is F, Cl or Br), $OCF_3$, CN, COOR (R is lower alkyl), phenyl, lower alkoxy, $NO_2$ or $SO_2R$ (R is lower alkyl) and at least one of $X_1$, $X_2$ and $X_3$ is other than H; and Y is COOR or carboxy;
is nitrated to give a product of the formula:

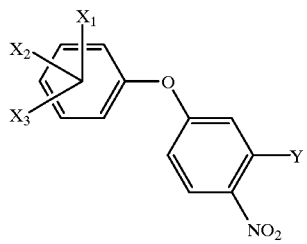

wherein $X_1$, $X_2$, $X_3$ and Y are as defined above.

The nitration is carried out using as nitrating agent a mixture of nitric and sulphuric acids in an organic solvent such as dichloromethane. The desirability of keeping the reaction system anhydrous by the addition of acetic anhydride is stressed as the authors of GB-A-2103214 state that this makes it possible to improve the selectivity with respect to acifluorfen (the desired nitrated product). The recommended ratio of starting material:solvent:acetic anhydride is 1:2.66:1.4. The reaction is conducted at a temperature of 45° C. and left for 3 hours. After this, the reaction mixture is allowed to stand so that the organic and aqueous phases separate and then the organic solvent is removed by distillation.

However, the present inventors have found that the use of reaction conditions suggested lead to various problems which do not seem to have been appreciated by the authors of the prior art document. In particular, although the use of acetic anhydride does, in some respects, improve the selectivity of the reaction, the relationship between the concentration of acetic anhydride and selectivity is more complex than the authors of GB-A-2103214 appear to have realised and, therefore, the amount of acetic anhydride in the reaction mixture must be carefully controlled in order to obtain a suitable product mixture.

Therefore in the present invention there is provided a process for the preparation of a compound of general formula I:

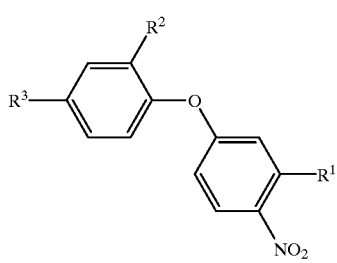

wherein:
  $R^1$ is hydrogen or $C_1$–$C_6$ alkyl, $C_2$–$C_6$ alkenyl or $C_2$–$C_6$ alkynyl, any of which may optionally be substituted with one or more substituents selected from halogen and OH; or $COOR^4$, $COR^6$, $CONR^4R^5$ or $CONHSO_2R^4$;
  $R^4$ and $R^5$ are each independently hydrogen or $C_1$–$C_4$ alkyl optionally substituted with
  one or more halogen atoms;
  $R^6$ is a halogen atom or a group $R^4$;
  $R^2$ is hydrogen or halo;
  $R^3$ is $C_1$–$C_4$ alkyl, $C_2$–$C_4$ alkenyl or $C_2$–$C_4$ alkynyl, any of which may optionally be substituted with one or more halogen atoms; or halo;

the process comprising reacting a compound of general formula II:

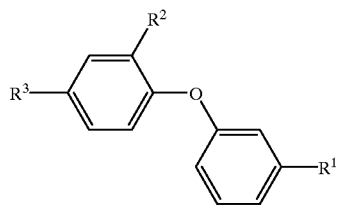

wherein $R^1$, $R^2$ and $R^3$ are as defined for general formula I;
  with a nitrating agent comprising nitric acid or a mixture of nitric and sulphuric acids in the presence of an organic solvent and in the presence of acetic anhydride, characterised in that the molar ratio of acetic anhydride to compound of general formula II is from about 1:1 to 3:1.

These reaction conditions give the advantage that the proportion of the required isomer is maximised whilst not causing too great a reduction in the yield of the product or too great an increase in operating costs.

In the context of the present invention, compounds of general formula I are designated 4-nitro isomers. The 2-nitro isomers referred to above have the general formula:

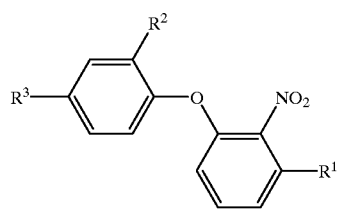

Other mono-nitro isomers which may be produced in the nitration reaction include the 6-nitro isomer:

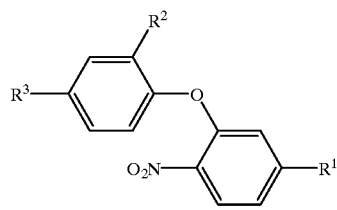

There are also three different dinitro isomers which may be present.

In the context of the present invention, the term "$C_1$–$C_6$ alkyl" refers to a saturated straight or branched hydrocarbon chain containing from 1 to 6 carbon atoms. Examples include methyl, ethyl, n-propyl, t-butyl, n-pentyl and n-hexyl. The term "$C_1$–$C_4$ alkyl" is a subset of $C_1$–$C_6$ alkyl and refers to an alkyl group having up to 4 carbon atoms.

The term "$C_2$–$C_6$ alkenyl" refers to a straight or branched hydrocarbon chain containing from 2 to 6 carbon atoms and having at least one double bond. Examples include ethenyl, allyl, propenyl and hexenyl. The term "$C_2$–$C_4$ alkenyl" is a subset of $C_2$–$C_6$ alkenyl and refers to an alkenyl group having up to 4 carbon atoms.

The term "$C_2$–$C_6$ alkynyl" refers to a straight or branched hydrocarbon chain containing from 2 to 6 carbon atoms and having at least one triple bond. Examples include ethynyl, propynyl and hexynyl. The term "$C_2$–$C_4$ alkynyl" is a subset of $C_2$–$C_6$ alkynyl and refers to an alkynyl group having up to 4 carbon atoms.

The term "halogen" refers to fluorine, chlorine, bromine or iodine and the corresponding term "halo" refers to fluoro, chloro, bromo or iodo.

The reaction conditions of the present invention are particularly advantageous since they maximise the amount of the required 4-nitro isomer in the product mixture. Surprisingly, it has been found by the present inventors that the relationship between the presence of acetic anhydride and the isomer ratio of the product mixture is not as simple as it appears from a reading of GB-A-2103214. This document suggests that the presence of acetic anhydride is beneficial but does not suggest that the amount present needs to be limited. The present inventors have found, however, that although the proportion of dinitro isomers (1) and (2) in the product mixture decreases as the amount of acetic anhydride is increased, the proportion of the 2-nitro impurity increases. This is a particular concern since the 2-nitro isomer is especially difficult to separate from the 4-nitro isomer and so, clearly, it is important to keep its concentration in the product mixture as low as possible. For this reason, the present inventors have found that it is not desirable to increase the acetic anhydride:compound II ratio to greater than about 3:1.

Additionally, the present inventors have discovered that the reaction temperature plays a significant role in determining the proportions of the various mono-nitrated isomers with a greater proportion of the required isomer being produced as the reaction temperature is reduced. The reaction temperature, too is a compromise since, clearly, it would not be economically viable to operate a reaction if the temperature were below a certain level because of the amount of cooling required. The decrease with temperature of the proportion of the 2-nitro and 6-nitro isomers in the product mixture does not seem to have been appreciated by the authors of GB-A-2103214 who recommended a reaction temperature of about 45° C. The present inventors have found that the amount of the 2-nitro isomer present in the product mixture when the reaction temperature is 45° C. is more than 12 parts per hundred whereas, when the reaction temperature is reduced to 10° C., the amount of 2-nitro isomer in the product mixture is reduced to 10 or 11 parts per hundred. This difference may affect any subsequent purification process and may be very significant when costing a large scale manufacturing process. The preferred temperature range for the process of the present invention is from about −15 to 15° C., more preferably −10 to 10° C.

It has also been found that the formation of the undesired isomers can be further reduced by increasing the concentration of the reactants in the solvent solution. In particular, it is advantageous to have a weight ratio of solvent to compound of formula II (including any isomers present) of no greater than 4.25:1 and it is preferred that the ratio is from 1:1 to 2.5:1.

The reaction may be carried out in any suitable solvent and examples of solvents which may be used include halogenated solvents such as dichloromethane (DCM), ethylene dichloride (EDC), chloroform, tetrachloroethylene (perklone) and dichlorobenzotrifluoride (DCBTF). Alternatively, solvents such as acetic acid, acetonitrile, ethers such as tetrahydrofuran (THF) or dioxane, sulpholane, nitrobenzene, nitromethane, liquid sulphur dioxide or liquid carbon dioxide may all be used successfully in the reaction.

Perklone is a particularly useful solvent for the process of the present invention since, under equivalent reaction conditions, perklone reactions give about 30% less of the 2- and 6-nitro isomers than reactions carried out in EDC or DCM under otherwise identical conditions. There are also indications that the yield of the reaction is increased when perklone is the solvent of choice.

As already mentioned, the nitrating agent used is nitric acid or, preferably, a mixture of nitric and sulphuric acids. A mixture of nitric and sulphuric acids may contain, for example, from about 30 to 45% of pure nitric acid, more typically from about 30 to 35% pure nitric acid.

When the chosen nitrating agent is a mixed acid, it will typically be added to the reaction mixture over a period of about 30 minutes to 15 hours. The rate of addition will, however vary according to the reaction solvent which is chosen with addition over about 1 to 6 hours, or preferably 2 to 4 hours, being appropriate for many solvents, for example EDC and DCM.

When the reaction is conducted in perklone, however, the rate of reaction is usually somewhat lower than for reactions conducted in other solvents such as EDC or DCM and so it is often advantageous to add the nitrating agent more slowly, for example over a period of from 5 to 15 hours, or, more preferably, 6 to 12 hours.

When both nitric and sulphuric acids are using in the process of the invention it is possible to further reduce the level of over nitration by adding these acids sequentially to the reaction mixture. It has been found particularly advantageous to add the sulphuric acid to a mixture of the compound of formula II and acetic anhydride in the chosen organic solvent, followed by addition of the nitric acid. When a sequential addition of the sulphuric and nitric acids is used the nitric acid is preferably greater than about 90% strength. The molar ratio of sulphuric acid: compound of general formula II used in the reaction will generally be up to 1.5:1, however a ratio of sulphuric acid:compound of general formula II of from 0.1:1 to 0.3:1 is preferred.

Although the process of the invention may be used for the preparation of any compound of general formula I, it is especially preferred that $R^2$ is chloro and $R^3$ is trifluoromethyl. Particularly preferred compounds of general formula I are those in which $R^1$ is COOH or $CONHSO_2CH_3$. These compounds are 5-(2-chloro-α,α,α-trifluoro-4-tolyloxy)-2-nitrobenzoic acid (acifluorfen) and 5-(2-chloro-α,α,α-trifluoro-4-tolyloxy)-N-methanesulphonyl-2-nitrobenzamide (fomesafen), both of which are potent herbicides.

In addition to being a herbicide in its own right, acifluorfen may also serve as an intermediate in the synthesis of fomesafen. The acifluorfen may be converted to the acid chloride which may then be reacted with methane sulphonamide to give fomesafen. Both of these steps may be carried out by conventional methods, for example as set out in EP-A-0003416.

The invention will now be further described by way of the following examples in which the following abbreviations are used:

DCM—dichloromethane;
EDC—ethylene dichloride;
pph—parts per hundred;
$Ac_2O$ Acetic anhydride;
HPLC—high performance liquid chromatography.

In the examples, the term "mixed acid" refers to a mixture containing 33.6% nitric acid and 66.4% sulphuric acid. The molar quantities given are the moles of nitric acid in the mixture.

Example 1

General Method for Nitration of 3-(2-chloro-α,α,α-trifluoro-4-tolyloxy)benzoic acid in Dichloromethane to Yield Acifluorfen a) Nitration

Ac$_2$O (see Tables I and II for amounts) was added to 3-(2-chloro-α,α,α-trifluoro-4-tolyloxy)benzoic acid (I, R$^1$ is COOH, R$^2$ is chloro, R$^3$ is trifluoromethyl) (20 g, 0.063 mol) in dichloromethane (54 g, 0.635 mol) and the mixture stirred and heated to 40° C. to dissolve the starting material. The mixture was then cooled to the appropriate reaction temperature (during which time any crystallisation of the starting material was observed). Mixed acid (13 g, 0.069 mol) was added dropwise over 2 hours and the reaction monitored by HPLC for the completion of the reaction. Further additions of mixed acid were made to reduce the level of starting material to about 1 pph.

b) Work-Up

The reaction mixture was washed three times as follows:

wash 1—water (30 ml) was added and the mixture washed at approximately 38° C. and the aqueous layer separated;

wash 2—water (25 ml) was added and the mixture washed at approximately 38° C. and the aqueous layer separated;

wash 3—water (25 ml) was added and the mixture washed at approximately 38° C. and the aqueous layer separated.

Water (80 ml) was then added and the mixture heated to 38° C. and sodium hydroxide (47% solution, 6.4 g, 0.076 mol) added to basify the mixture to pH 10–11. The mixture was heated to distil off the DCM in order to afford a solution of acifluorfen sodium salt. The solution was cooled to room temperature and transferred with the aid of a minimum amount of water to a bottle in order for the solution to be weighed and analysed.

The results for various amounts of Ac$_2$O and various reaction temperatures are shown in Table I (see Experiments 1 to 11).

EXAMPLE 2

General Method for Nitration of 3-(2-chloro-α,α,α-trifluoro-4-tolyloxy)benzoic acid in Ethylene Dichloride to Yield Acifluorfen a) Nitration

Ac$_2$O (see Tables I and II for amounts) was added to 3-(2-chloro-α,α,α-trifluoro-4-tolyloxy)benzoic acid (20 g, 0.063 mol) in EDC (54 g, 0.545 mol) and the mixture stirred and heated to 40° C. to dissolve the starting material. The mixture was then cooled to the appropriate reaction temperature (during which time any crystallisation of the starting material was observed). Mixed acid (33.6%, 13 g, 0.069 mol) was added dropwise over a period of 2 hours and the reaction monitored by HPLC for the completion of the reaction. Further additions of mixed acid were made to reduce the level of starting material to about 1 pph.

b) Work-Up

The reaction mixture was washed three times as follows:

wash 1—water (30 ml) was added and the mixture washed at approximately 70° C. and the aqueous layer separated;

wash 2—water (25 ml) was added and the mixture washed at approximately 70° C. and the aqueous layer separated;

wash 3—water (25 ml) was added and the mixture washed at approximately 70° C. and the aqueous layer separated.

Water (80 ml) was then added and the mixture heated to 80° C. and sodium hydroxide (47% solution, 6.4 g, 0.076 mol) added to basify the mixture to pH 10–11. The mixture was allowed to separate and the EDC layer was removed. Traces of residual EDC were then removed by distillation to afford a solution of acifluorfen sodium salt. The solution was cooled to room temperature and transferred with the aid of a minimum amount of water to a bottle in order for the solution to be weighed and analysed.

EXAMPLE 3

General Method for Nitration of 3-(2-chloro-α,α,α-trifluoro-4-tolyloxy)benzoic acid in Perklone to Yield Acifluorfen

The general method and quantities of reagents were exactly as described for Examples 1 and 2 except that the solvent used was perklone.

The results for Experiments 1 to 45 which were conducted according to the general methods of Examples 1 to 3 are set out in Tables I and II below. In these experiments, the amounts of Ac$_2$O, the reaction temperature, the solvent and the quantity of solvent were varied in order to determine the optimum reaction conditions. In each of these experiments, 20 g crude starting material was used containing 84.3% 3-(2-chloro-α,α,α-trifluoro-4-tolyloxy)benzoic acid. In each of the experiments described in Table I, the amount of solvent used was 54.0 g but for the experiments detailed in Table II, the quantity of solvent was varied. In Tables I and II, the term "reactant" refers to 3-(2-chloro-α,α,α-trifluoro-4-tolyloxy)benzoic acid.

TABLE I

| Exp | Solvent | Reaction Temp ° C. | Ac$_2$O use (mol/mol) | HNO$_3$ use (mol/mol) | Product Yield % | 2'-nitro | 6'-nitro | dinitro 1 | dintro 2 | dintro 3 | Total dinitro | Reactant | Impurity Yield % |
|---|---|---|---|---|---|---|---|---|---|---|---|---|---|
| | | | | | | pph | | | | | | | |
| 1 | DCM | −10 | 1.40 | 1.10 | 82.1 | 8.62 | 4.89 | 0.70 | 1.73 | 0.00 | 2.43 | 0.00 | 13.09 |
| 2 | DCM | 0 | 1.40 | 1.10 | 82.4 | 9.39 | 5.56 | 1.52 | 2.12 | 0.53 | 4.17 | 1.30 | 16.83 |
| 3 | DCM | 10 | 1.40 | 1.10 | 85.2 | 10.36 | 6.00 | 0.83 | 2.07 | 0.46 | 3.36 | 0.00 | 16.80 |
| 4 | DCM | −10 | 2.00 | 1.10 | 85.9 | 9.01 | 5.37 | 0.81 | 1.35 | 0.00 | 2.15 | 0.00 | 14.20 |
| 5 | DCM | 0 | 2.00 | 1.10 | 86.1 | 9.58 | 5.79 | 0.81 | 1.77 | 0.39 | 2.96 | 0.00 | 15.78 |
| 6 | DCM | 10 | 2.00 | 1.10 | 84.5 | 10.58 | 6.33 | 0.58 | 0.99 | 0.35 | 1.92 | 0.00 | 15.91 |
| 7 | DCM | −10 | 3.00 | 1.10 | 86.5 | 9.79 | 5.63 | 0.60 | 1.38 | 0.25 | 2.23 | 0.46 | 15.67 |
| 8 | DCM | 0 | 3.00 | 1.10 | 84.3 | 10.56 | 6.17 | 0.52 | 0.90 | 0.00 | 1.42 | 0.00 | 15.30 |
| 9 | DCM | 10 | 3.00 | 1.10 | 83.3 | 11.15 | 6.51 | 0.50 | 0.52 | 0.50 | 1.51 | 1.46 | 17.18 |
| 10 | DCM | 0 | 1.00 | 1.29 | 82.7 | 10.20 | 5.02 | 0.72 | 1.42 | 0.98 | 3.12 | 4.26 | 18.68 |
| 11 | DCM | 0 | 0.50 | 1.42 | 81.7 | 13.23 | 5.48 | 0.84 | 3.67 | 0.71 | 5.23 | 0.00 | 19.57 |

TABLE I-continued

| Exp | Solvent | Reaction Temp ° C. | Ac₂O use (mol/mol) | HNO₃ use (mol/mol) | Product Yield % | pph | | | | | | | Impurity Yield % |
|---|---|---|---|---|---|---|---|---|---|---|---|---|---|
| | | | | | | 2'-nitro | 6'-nitro | dinitro 1 | dintro 2 | dintro 3 | Total dinitro | Reactant | |
| 12 | EDC | −10 | 1.40 | 1.10 | 86.5 | 8.85 | 4.64 | 0.55 | 1.08 | 0.32 | 1.95 | 1.52 | 14.67 |
| 13 | EDC | 0 | 1.40 | 1.10 | 81.6 | 9.03 | 5.06 | 0.61 | 1.92 | 0.47 | 3.00 | 1.00 | 14.76 |
| 14 | EDC | 10 | 1.40 | 1.20 | 84.6 | 10.21 | 5.45 | 0.93 | 1.74 | 0.54 | 3.21 | 0.00 | 15.96 |
| 15 | EDC | −10 | 2.00 | 1.10 | 84.2 | 8.72 | 4.77 | 0.48 | 0.85 | 0.00 | 1.33 | 0.00 | 12.47 |
| 16 | EDC | 0 | 2.00 | 1.10 | 83.9 | 9.09 | 5.31 | 0.65 | 1.66 | 1.97 | 4.28 | 0.00 | 15.66 |
| 17 | EDC | 10 | 2.00 | 1.10 | 84.2 | 10.21 | 5.90 | 0.44 | 0.81 | 0.49 | 1.74 | 0.00 | 15.04 |
| 18 | EDC | −10 | 3.00 | 1.10 | 85.4 | 9.05 | 4.74 | 0.48 | 0.76 | 0.34 | 1.58 | 1.18 | 14.13 |
| 19 | EDC | 0 | 3.00 | 1.10 | 83.3 | 10.14 | 5.65 | 0.61 | 0.90 | 0.33 | 1.84 | 0.00 | 14.69 |
| 20 | EDC | 10 | 3.00 | 1.10 | 81.6 | 11.12 | 6.21 | 0.48 | 0.25 | 0.52 | 1.25 | 2.08 | 16.86 |
| 21 | EDC | 0 | 1.00 | 1.20 | 80.5 | 9.83 | 4.73 | 0.70 | 1.80 | 1.15 | 3.66 | 5.88 | 19.41 |
| 22 | EDC | 0 | 0.50 | 1.21 | 76.5 | 13.58 | 5.65 | 0.74 | 2.74 | 2.80 | 6.29 | 6.56 | 24.55 |
| 23 | EDC | 10 | AcOH | 1.10 | 56.9 | 15.61 | 6.80 | 1.00 | 1.31 | 0.00 | 2.31 | 43.60 | 38.89 |
| 24 | perklone | −10 | 1.40 | 1.20 | 82.1 | 5.28 | 2.54 | 0.73 | 2.94 | 0.83 | 4.50 | 9.16 | 17.64 |
| 25 | perklone | 0 | 1.40 | 1.16 | 84.7 | 6.36 | 3.06 | 0.56 | 3.43 | 3.61 | 7.60 | 3.39 | 17.29 |
| 26 | perklone | 10 | 1.40 | 1.22 | 82.1 | 7.58 | 3.68 | 0.51 | 3.58 | 1.96 | 6.05 | 2.88 | 16.58 |
| 27 | perklone | −10 | 2.00 | 1.18 | 87.5 | 5.46 | 2.82 | 0.61 | 3.38 | 1.16 | 5.15 | 3.25 | 14.59 |
| 28 | perklone | 0 | 2.00 | 1.20 | 85.3 | 7.03 | 3.61 | 0.59 | 3.44 | 1.96 | 5.98 | 1.86 | 15.76 |
| 29 | perklone | 10 | 2.00 | 1.27 | 84.5 | 7.56 | 3.89 | 0.61 | 3.86 | 2.85 | 7.33 | 1.46 | 17.10 |
| 30 | perklone | 10 | 3.00 | 1.24 | 85.9 | 7.01 | 3.46 | 0.71 | 0.22 | 0.41 | 1.34 | 1.08 | 11.07 |
| 31 | perklone | 0 | 3.00 | 1.21 | 85.9 | 6.29 | 3.66 | 0.66 | 4.49 | 1.84 | 7.00 | 1.07 | 15.47 |
| 32 | perklone | 10 | 3.00 | 1.16 | 82.2 | 8.86 | 4.83 | 0.59 | 1.79 | 1.54 | 3.91 | 0.00 | 14.47 |
| 33 | perklone | 0 | 1.40 | 1.13 | 80.0 | 6.35 | 3.33 | 0.73 | 2.99 | 0.44 | 4.15 | 9.37 | 18.57 |
| 34 | perklone | 10 | 1.40 | 1.13 | 83.0 | 7.80 | 4.02 | 0.70 | 3.55 | 0.75 | 5.01 | 3.67 | 17.01 |
| 35 | perklone | 0–5 | 3.00 | 1.20 | 85.4 | 8.07 | 4.43 | 0.85 | 4.14 | 0.90 | 5.89 | 0.00 | 15.72 |
| 36 | perklone | 0–5 | 3.00 | 1.20 | 84.6 | 7.94 | 4.43 | 0.81 | 3.35 | 1.09 | 5.25 | 0.00 | 14.90 |

TABLE II

| Exp | Solvent | Solvent usage (g) | Reaction Temp ° C. | Ac₂O use (mol/mol) | HNO₃ use (mol/mol) | Product Yield % | pph | | | | | | | Impurity Yield % |
|---|---|---|---|---|---|---|---|---|---|---|---|---|---|---|
| | | | | | | | 2'-nitro | 6'-nitro | dinitro 1 | dintro 2 | dintro 3 | Total dinitro | Reactant | |
| 37 | DCM | 27.0 | −10 | 2.00 | 1.10 | 86.1 | 8.66 | 5.21 | 0.45 | 0.61 | 0.27 | 1.34 | 1.51 | 14.39 |
| 38 | DCM | 54.0 | −10 | 2.00 | 1.10 | 85.9 | 9.01 | 5.37 | 0.81 | 1.35 | 0.00 | 2.15 | 0.00 | 14.20 |
| 38 | DCM | 100.0 | −10 | 2.00 | 1.10 | 83.9 | 9.38 | 5.44 | 0.76 | 1.68 | 0.45 | 2.89 | 0.00 | 14.85 |
| 40 | EDC | 27.0 | −10 | 2.00 | 1.11 | 85.8 | 8.19 | 4.49 | 1.38 | 2.23 | 0.29 | 3.90 | 1.70 | 15.68 |
| 41 | EDC | 54.0 | −10 | 2.00 | 1.10 | 84.2 | 8.72 | 4.77 | 0.48 | 0.85 | 0.00 | 1.33 | 0.00 | 12.47 |
| 42 | EDC | 100.0 | −10 | 2.00 | 1.10 | 83.7 | 9.20 | 4.68 | 0.62 | 1.07 | 0.43 | 2.12 | 0.00 | 13.38 |
| 43 | perklone | 27.0 | −10 | 2.00 | 1.27 | 85.7 | 5.77 | 2.97 | 0.76 | 4.15 | 0.62 | 5.52 | 2.07 | 14.00 |
| 44 | perklone | 54.0 | −10 | 2.00 | 1.18 | 87.5 | 5.46 | 2.82 | 0.61 | 3.38 | 1.16 | 5.15 | 3.25 | 14.59 |
| 45 | perklone | 100.0 | −10 | 2.00 | 1.27 | 84.9 | 5.28 | 2.85 | 0.70 | 4.75 | 0.62 | 6.07 | 2.45 | 14.14 |

The results presented in Table I demonstrate the effects on the concentration of impurities in the final product of changing the molar ratio of Ac$_2$O to starting material, temperature and the solvent.

Firstly, the effect of Ac$_2$O:starting material can be seen from a comparison of the results for Experiments 11, 10, 2, 5 and 8 of Table I, all of which were conducted using DCM as solvent and at a temperature of 0° C. The table shows that while the total concentration of dinitro impurities in the product mixture fell as the ratio of Ac$_2$O:starting material increased, the amounts of the 2-nitro and 6-nitro isomers in the product mixture did not follow this pattern. Thus, for Ac$_2$O ratios of 0.5, 1.0, 1.4, 2.0 and 3.0, the amounts of 2-nitro isomer present in the product mixture expressed in pph were 13.23, 10.2, 9.39, 9.58 and 10.56 whilst corresponding values for the 6-nitro isomer were 5.48, 5.02, 5.56, 5.79 and 6.17. Since the 2- and 6-nitro isomers are more difficult to separate from acifluorfen than the dinitro isomers, it is obviously preferable to minimise the production of these mononitro isomers and, thus, it can be seen that, for optimum performance, the molar ratio of Ac$_2$O to starting material must be maintained at from about 1:1 to 3:1.

The effect of temperature can be seen by comparing, for example, the results of Experiments 1 to 3 or 12 to 14 or 24 to 26. It is clear that, in general, the amounts of all the impurities in the product mixture increase as the temperature increases.

Solvent effects are also apparent from Table I and it can be seen that, whilst the amounts of 2-nitro and 6-nitro impurities in the product mixtures are similar for DCM and EDC, they are about 32% lower when Perklone is used as the solvent. Perklone thus appears to be a particularly favourable solvent for use in the present invention.

The results of experiments to test the effect of varying the amount of solvent present in the reaction mixture are shown in Table II. From this table it can be seen that, in general, the amounts of 2-nitro and 6-nitro isomers present in the product mixture increase as the reaction mixture becomes more dilute.

EXAMPLE 4

Nitration of 3-(2-chloro-α,α,α-trifluoro-4-tolyloxy)-N-(methylsulphonyl)benzamide in Dichloromethane to Yield Fomesafen 3-(2-Chloro-α,α,α-trifluoro-4-tolyloxy)-N-(methylsulphonyl)benzamide (10.4 g, 0.0264 mol) was dispersed in DCM (25.9 g) with stirring. Ac$_2$O (11.4 g, 98%, 0.110 mol) was added to the mixture over about 30 min maintaining the temperature at about 20° C.

Mixed nitric and sulphuric acids (32.6% nitric acid, 0.0317 mol) were added slowly over about 45 min, following which the reaction mixture was heated to about 40° to 45° C. for 3 hours. The reaction mass was washed with water and the solvent was removed by distillation to give 10.4 g, 85.2% yield of the required product, fomesafen. The product mixture also contained 6.8 pph 2-nitro isomer and 5.3 pph 6-nitro isomer.

EXAMPLE 5

Nitration of 3-(2-chloro-α,α,α-trifluoro-4-tolyloxy)benzoic Acid Sodium Salt in Perklone to Yield Acifluorfen Using Sequential Addition of Sulphuric Acid and Nitric Acid 3-(2-Chloro-α,α,α-trifluoro-4-tolyloxy) benzoic acid sodium salt (550 g, of a 36.4% solution) was added to a nitration vessel followed by perklone (734 g). The mixture was heated to 80° C. with agitation and 98% sulphuric acid (63 g) added slowly to give a pH of 2. The mixture was allowed to separate and the aqueous layer removed. The solvent layer was washed with water (100 g) at 80° C. and after separation was dried by azeotropic removal of water up to a batch temperature of 120° C.

The solution of 3-(2-chloro-α,α,α-trifluoro-4-tolyloxy) benzoic acid in perklone was cooled to 60° C. and Ac$_2$O (195 g) and 98% sulphuric acid (63 g) added with stirring. The mixture was cooled to 0° C. and 90% nitric acid (53 g) was added at 0° C. over 3½ hours with vigorous agitation. The resulting mixture was stirred for 1 hour at 0° C. and then water (190 g) was added. The mixture was heated to 80° C. and then allowed to settle. The aqueous layer was removed and the solvent layer washed with water (162 g) at 80° C. Approximately 360 g of perklone was removed by direct distillation and the remainder removed by azeotropic distillation with added water. Once all the perklone had been removed the resulting mixture of molten acifluorfen and water was treated with sodium hydroxide (158 g of a 15% solution) at 90° C. Once the addition was complete the mixture was cooled to 45° C. and sodium hydroxide (39 g of a 15% solution) added to give a pH of 7–9. The resulting 40% solution of acifluorfen sodium salt in water was then allowed to cool, yield 85%.

A sample of the product was acidified and the precipitated acifluorfen acid was filtered, washed and dried and gave the following analysis by HPLC using authentic standards for analysis of acifluorfen and the nitrated isomers:

acifluorfen 76.5%

Impurities expressed as % weight×100/% acifluorfen:

| | |
|---|---|
| 2'-nitro isomer | 7.5 |
| 6'-nitro isomer | 3.9 |
| isomer from reactant | 7.0 |
| reactant | 1.5 |
| total dinitro isomers | 1.1 |
| trinitro | 0.4 |

We claim:

1. A process for the preparation of a compound of general formula I:

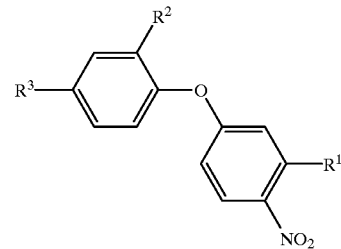

wherein:

R$^1$ is hydrogen or C$_1$–C$_6$ alkyl, C$_2$–C$_6$ alkenyl or C$_2$–C$_6$ alkynyl, any of which may optionally be substituted with one or more substituents selected from halogen and OH; or COOR$^4$, COR$^6$, CONR$^4$R$^5$ or CONHSO$_2$R$^4$;

R$^4$ and R$^5$ are each independently hydrogen or C$_1$–C$_4$ alkyl optionally substituted with one or more halogen atoms;

R$^6$ is a halogen atom or a group R$^4$;

R$^2$ is hydrogen or halo;

R$^3$ is C$_1$–C$_4$ alkyl, C$_2$–C$_4$ alkenyl or C$_2$–C$_4$ alkynyl, any of which may optionally be substituted with one or more halogen atoms; or halo;

the process comprising reacting a compound of general formula II:

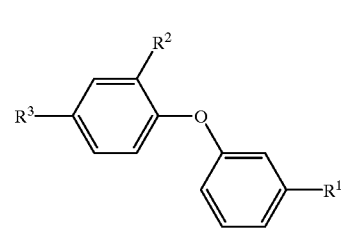

wherein R$^1$, R$^2$ and R$^3$ are as defined for general formula I;

with a nitrating agent comprising a mixture of nitric and sulphuric acids in the presence of an organic solvent and in the presence of acetic anhydride, wherein the molar ratio of acetic anhydride to compound of general formula II is from about 1:1 to 3:1 and the organic solvent is tetrachloroethylene (perklone) and wherein the sulphuric and nitric acids are added sequentially to the reaction mixture.

2. A process as claimed in claim 1, wherein the weight ratio of solvent to compound of formula II (including any isomers present) is no greater than 4.25:1.

3. A process as claimed in claim 2, wherein the weight ratio of solvent to compound of formula II (including any isomers present) is from 1:1 to 2.5:1.

4. A process as claimed in claim 1, wherein the nitrating agent is added to the reaction mixture over a period of about 30 minutes to 15 hours.

5. A process according to claim 1, wherein the ratio of sulphuric acid:compound of formula II is from 0.1:1 to 0.3:1.

6. A process as claimed in claim 1, wherein the reaction is performed at a temperature of from about −15° C. to 15° C.

7. A process as claimed in claim 6, wherein the reaction is performed at a temperature of from −10° C. to 10° C.

8. A process as claimed in claim 1, wherein, in the compound of general formula I, $R^2$ is chloro and $R^3$ is trifluoromethyl.

9. A process as claimed in claim 1, wherein the compound of general formula I is 5-(2-chloro-α,α,α-trifluoro-4-tolyloxy)-2-nitrobenzoic acid (acifluorfen) or 5-(2-chloro-α,α,α-trifluoro-4-tolyloxy)-N-methanesulphonyl-2-nitrobenzamide (fomesafen).

10. A process as claimed in claim 1, wherein the compound of general formula I is acifluorfen and which further comprises the steps of converting the acifluorfen to its acid chloride and treating the acid chloride with methane sulphonamide to give fomesafen.

11. A process as claimed in claim 1, wherein the nitrating agent is a mixture of nitric and sulphuric acids containing from 30 to 45% of pure nitric acid.

12. A process as claimed in claim 1 wherein the nitric acid is greater than 90% strength.

* * * * *